US009247864B2

(12) United States Patent
Sakamoto

(10) Patent No.: US 9,247,864 B2
(45) Date of Patent: Feb. 2, 2016

(54) CABLE CONNECTOR FOR ENDOSCOPE APPARATUS AND METHOD OF PRODUCING ENDOSCOPE APPARATUS

(71) Applicant: FUJIFILM Corporation, Tokyo (JP)

(72) Inventor: Toshio Sakamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 352 days.

(21) Appl. No.: 13/796,907

(22) Filed: Mar. 12, 2013

(65) Prior Publication Data

US 2013/0244456 A1    Sep. 19, 2013

(30) Foreign Application Priority Data

Mar. 13, 2012  (JP) .................................. 2012-055536

(51) Int. Cl.
  *A61B 1/04*  (2006.01)
  *H01R 12/00*  (2006.01)
  *A61B 1/00*  (2006.01)
  *A61B 1/05*  (2006.01)

(52) U.S. Cl.
  CPC .............. *A61B 1/00124* (2013.01); *A61B 1/05* (2013.01); *Y10T 29/49174* (2015.01)

(58) Field of Classification Search
  CPC ...... A61B 1/00124; A61B 1/005; A61B 1/05; A61B 1/00; H01R 12/712; H01R 12/53; H01R 12/721; H01R 12/71
  USPC .............................. 600/132; 439/55, 76.1, 81
  See application file for complete search history.

(56) References Cited

U.S. PATENT DOCUMENTS

| 5,957,727 | A | * | 9/1999 | Page, Jr. ................... 439/607.58 |
| 6,319,197 | B1 | * | 11/2001 | Tsuji et al. .................... 600/132 |
| 2003/0222325 | A1 | * | 12/2003 | Jacobsen et al. ............... 257/432 |
| 2005/0143658 | A1 | | 6/2005 | Saiga |
| 2005/0143659 | A1 | | 6/2005 | Saiga |

(Continued)

FOREIGN PATENT DOCUMENTS

| CN | 101102714 A | 1/2008 |
| JP | 2006-192202 A | 7/2006 |

OTHER PUBLICATIONS

Japanese Office Action for corresponding Japanese Application No. 2013-030180 dated Feb. 19, 2014 (with English translation).

(Continued)

*Primary Examiner* — John P Leubecker
*Assistant Examiner* — Arnaldo Torres Diaz
(74) *Attorney, Agent, or Firm* — Birch, Stewart, Kolasch & Birch, LLP

(57) ABSTRACT

An endoscope apparatus includes an elongated tube, a imaging unit in the elongated tube, and a cable structure, including plural signal lines, having first and second ends, the first end being connected to the imaging unit. A cable connector is connected with the second end, and couplable with a socket connector connectively. The cable connector includes a circuit board having a width in a manner passable through the elongated tube in an axial direction. A conductive land is formed on the circuit board, and coupled to the second end. A terminal pattern is formed on the circuit board, for connective coupling by reception in the socket connector. An advancing tip is formed on a front side of the circuit board in the axial direction, for initially advancing upon entry of the circuit board in the elongated tube, to enable the conductive land and the terminal pattern to pass safely.

17 Claims, 13 Drawing Sheets

(56) References Cited

U.S. PATENT DOCUMENTS

| | | | |
|---|---|---|---|
| 2006/0116550 A1* | 6/2006 | Noguchi et al. | 600/132 |
| 2006/0116552 A1* | 6/2006 | Noguchi et al. | 600/159 |
| 2006/0287576 A1* | 12/2006 | Tsuji et al. | 600/132 |
| 2007/0038023 A1* | 2/2007 | Uchimura et al. | 600/109 |
| 2007/0276182 A1* | 11/2007 | Adler et al. | 600/110 |
| 2008/0249363 A1 | 10/2008 | Nakamura et al. | |
| 2009/0268019 A1* | 10/2009 | Ishii et al. | 348/65 |
| 2012/0065469 A1* | 3/2012 | Allyn et al. | 600/109 |
| 2012/0202385 A1* | 8/2012 | Miyagi et al. | 439/626 |
| 2013/0244453 A1* | 9/2013 | Sakamoto | 439/55 |

OTHER PUBLICATIONS

Chinese Office Action dated Sep. 15, 2015, issued in corresponding Chinese Patent Application No. 201310079966.4 (with English Translation).

* cited by examiner

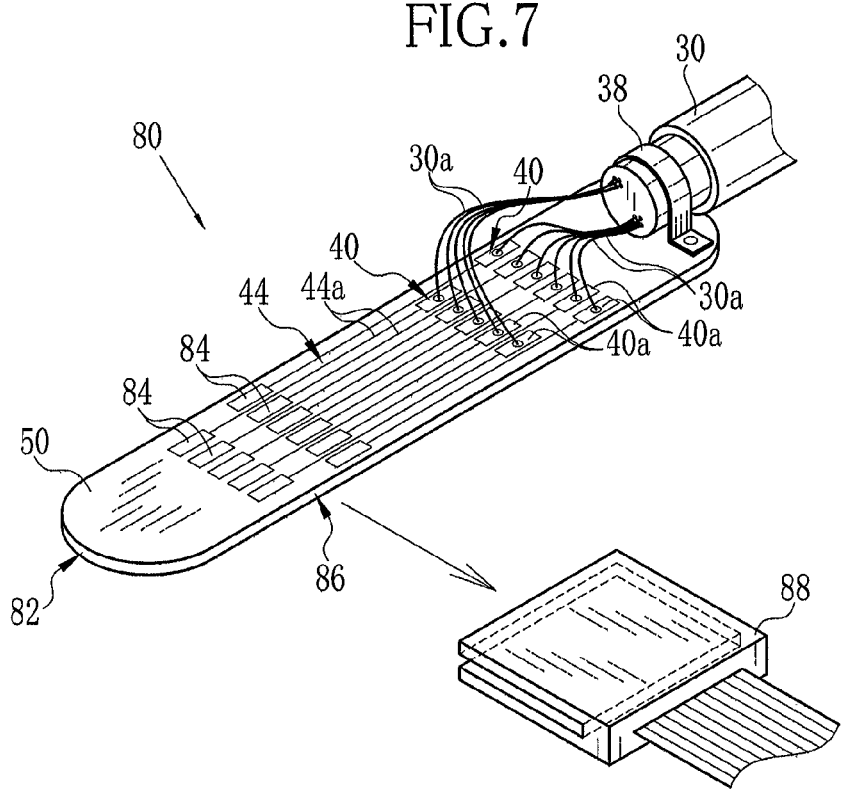
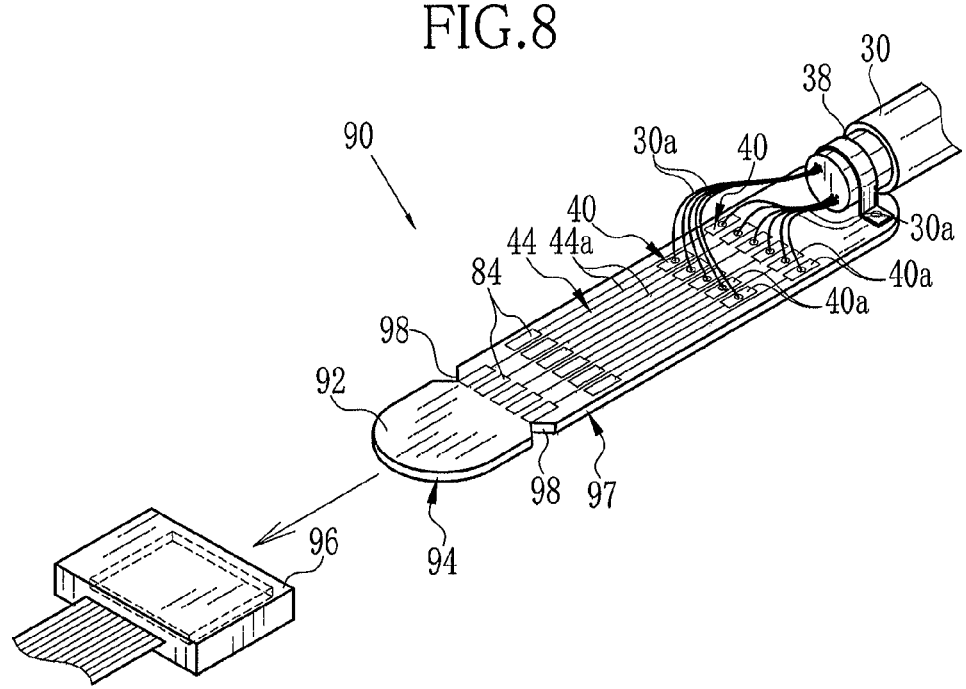

CABLE CONNECTOR FOR ENDOSCOPE APPARATUS AND METHOD OF PRODUCING ENDOSCOPE APPARATUS

BACKGROUND OF THE INVENTION

1. Field of the Invention

The present invention relates to a cable connector for an endoscope apparatus and a method of producing an endoscope apparatus. More particularly, the present invention relates to a cable connector for an endoscope apparatus, in which important elements of a circuit board can be safely moved for penetration in an elongated tube of the endoscope apparatus in an assembling operation, and a method of producing an endoscope apparatus.

2. Description Related to the Prior Art

An endoscope apparatus includes an elongated tube, a tip device and a circuit device or electrical device. The elongated tube is entered in a body cavity of a patient's body to be diagnosed. The tip device is disposed at a distal end of the elongated tube. The circuit device is contained in the tip device or disposed behind the tip device. Examples of the circuit device are a camera module, imaging unit or ultrasonic transducer. A cable structure is connected with the circuit device and extends in an axial direction. The cable structure includes numerous signal lines, which are connected to a control unit disposed in the outside of the body. The circuit device is controlled and driven by the control unit.

A flexible tube device is included in the elongated tube, and disposed to extend from the tip device. The tip device is apart originally separate from the flexible tube device. In the assembling operation, the circuit device is contained the tip device at first. The cable structure from the circuit device is passed through the flexible tube device. Then the flexible tube device is connected with the tip device.

The cable structure passes through the flexible tube device on the elongated tube. It is extremely difficult to connect each one of the signal lines in the cable structure to the control unit after passage through the flexible tube device. If the signal lines are connected with a mechanical part with a larger width than an inner diameter of the elongated tube, maintenance of the endoscope apparatus is very hard. This is because the cable structure can be disassembled from the flexible tube device only after cutting the signal lines from the mechanical part.

A cable connector or board connector at an end of the cable structure is disclosed in U.S. Pat. Pub. No. 2005/143,658 (corresponding to JP-A 2005-192640) and U.S. Pat. Pub. No. 2005/143,659 (corresponding to JP-A 2005-192639). The cable connector is in a plate shape and includes a land pattern, a terminal pattern and a wiring pattern. Signal lines of the cable structure are electrically coupled to the land pattern. The terminal pattern has plural terminals, and is couplable with a mating connector connectively. The wiring pattern electrically couples the land pattern to the terminals. The cable structure, in combination with the cable connector, is penetrated through the housing of the elongated tube by advancing the cable connector, to facilitate connective coupling and decoupling after the penetration of the cable structure.

However, in the documents, there is no suggestion of coping with collision of the cable connector with an inner surface of the elongated tube in the course of the penetration. A problem arises in possibility of occurrence of damages of the terminal pattern and the land pattern as important elements in the course of penetration in the elongated tube.

SUMMARY OF THE INVENTION

In view of the foregoing problems, an object of the present invention is to provide a cable connector for an endoscope apparatus, in which important elements of a circuit board can be safely moved for penetration in an elongated tube of the endoscope apparatus in an assembling operation, and a method of producing an endoscope apparatus.

In order to achieve the above and other objects and advantages of this invention, a cable connector for an endoscope apparatus is provided, the endoscope apparatus including an elongated tube disposed to extend in an axial direction, a circuit device incorporated in the elongated tube, and a cable structure, including plural signal lines, having first and second ends, the first end being connected to the circuit device, wherein the cable connector is connected with the second end, and couplable with a socket connector connectively. The cable connector includes a circuit board having a predetermined width in a manner passable through the elongated tube in the axial direction. A conductive land is formed on the circuit board, and coupled to the second end. A terminal pattern is formed on the circuit board, for connective coupling by reception in the socket connector. An advancing tip is formed on a front side of the circuit board in the axial direction, for initially advancing upon entry of the circuit board in the elongated tube, to enable the conductive land and the terminal pattern to pass safely.

Flexibility of the advancing tip is higher than flexibility of a portion of the circuit board on a rear side from the advancing tip.

The circuit device is an imaging unit for generating an image signal according to object light from a body cavity.

The advancing tip has a width decreasing in the axial direction.

The advancing tip includes a widest section, formed on a front side of the circuit board in the axial direction, and having a maximum width.

The advancing tip further includes a tapered section, formed on a front side of the widest section, and having a decreasing width.

In another preferred embodiment, the advancing tip includes a thickest section, formed on a front side of the circuit board in the axial direction, and having a maximum thickness.

The conductive land is disposed at a rear end of the circuit board in the axial direction.

Furthermore, a tear line is disposed in the circuit board on a rear side from the advancing tip, and adapted for tearing off the advancing tip after containment in the elongated tube.

A portion of the tear line has a lower strength than a remaining portion of the circuit board.

Furthermore, first and second notches are formed in respectively first and second longer side lines of the circuit board extending in the axial direction, and disposed at respectively ends of the tear line.

In one preferred embodiment, furthermore, a bend line is formed in the circuit board on a rear side from the advancing tip, wherein the advancing tip is overlapped on at least the terminal pattern by bending the circuit board along the bend line.

The terminal pattern includes plural terminals arranged on a longer side line of the circuit board extending in the axial direction.

Furthermore, a pair of cutouts are formed in a longer side line of the circuit board extending in the axial direction, so positioned that the terminal pattern is disposed therebetween, for preventing interference with a wall of the socket connector in coupling of the terminal pattern with the socket connector.

In still another preferred embodiment, furthermore, a first cutout is disposed in the circuit board on a rear side from the advancing tip, and formed in a first longer side line of the circuit board extending in the axial direction. A tear line is disposed to extend from the first cutout in a transverse direction of the circuit board, and adapted for tearing off the advancing tip after containment in the elongated tube. A second cutout is disposed in the circuit board on a rear side from the terminal pattern, formed in the first longer the line, for preventing interference with a wall of the socket connector in coupling of the terminal pattern with the socket connector.

In one preferred embodiment, the terminal pattern includes plural terminals arranged in a transverse direction of the circuit board.

Furthermore, an opening is formed in the circuit board between the advancing tip and the terminal pattern. The opening includes a first open area disposed to extend in a transverse direction of the circuit board. Second and third open areas are disposed to extend from respectively first and second ends of the first open area toward a rear side, and so positioned that the terminal pattern is disposed therebetween.

The endoscope includes a handle device, mounted on a proximal end of the elongated tube, for partially containing the cable structure. The cable structure includes a universal cable portion, disposed to extend further from the handle device in the axial direction, and having the second end.

Also, furthermore, a protection packaging is set on the circuit board before entry in the elongated tube, for covering and protecting at least the conductive land on the circuit board.

Furthermore, a guide surface is disposed on a rear side of the circuit board, formed in a direction to decrease a width in the axial direction, for smoothing passage through the elongated tube for disassembling the circuit board.

The terminal pattern is directed to the socket connector in a transverse direction of the circuit board and engaged therewith.

In another preferred embodiment, the terminal pattern is directed to the socket connector in the axial direction and engaged therewith.

Furthermore, a conductive pattern is formed on the circuit board and crosswise to the tear line. A residual portion of the conductive pattern along the tear line constitutes the terminal pattern after tearing off the advancing tip.

Also, a side edge of the terminal pattern extending in the axial direction is positioned to retreat from a longer side line of the circuit board in a transverse direction of the circuit board.

The tear line includes plural perforations arranged between a pair of longer side lines of the circuit board extending in the axial direction.

The tear line includes a slit formed in a first longer side line of the circuit board extending in the axial direction. Plural perforations are arranged between the slit and a second longer side line of the circuit board extending in the axial direction.

In one preferred embodiment, furthermore, a tear line is formed in the circuit board to extend between the advancing tip and the terminal pattern, and adapted to tear-off of the advancing tip after entry in the elongated tube. A spacer region is formed along a first longer side line of the circuit board on a rear side from the tear line, arranged with the terminal pattern in a transverse direction of the circuit board, for preventing the terminal pattern from being damaged. A separation line is disposed between the terminal pattern and the spacer region in the axial direction, and adapted to separation of the spacer region therefrom.

Furthermore, an unused region is disposed in the circuit board on a rear side from the terminal pattern, and positioned on the first longer side line. An auxiliary tear line is disposed to surround the unused region together with the first longer side line, for forming a cutout by tearing off the unused region from the circuit board.

In still another preferred embodiment, a residual region is formed in the circuit board on a rear side of the tear line by tear-off therewith, and is in a shape with a width decreasing in the axial direction.

Also, a producing method of producing an endoscope apparatus is provided, the endoscope apparatus including an elongated tube disposed to extend in an axial direction, and having a first longitudinal end on a distal side and a second longitudinal end on a proximal side, a circuit device incorporated in the elongated tube, a cable structure, including plural signal lines, having first and second ends, the first end being connected to the circuit device, and a cable connector, connected with the second end, and couplable with a socket connector electrically. The producing method includes a step of connecting the first end with the circuit device. The second end is connected with the cable connector. The cable connector is advanced into the first longitudinal end, wherein the cable connector includes a circuit board having a predetermined width in a manner passable through the elongated tube in the axial direction, a conductive land formed on the circuit board, and coupled to the second end, a terminal pattern, formed on the circuit board, for connective coupling by reception in the socket connector, and an advancing tip, formed on a front side of the circuit board in the axial direction, for initially advancing upon entry of the circuit board in the elongated tube, to enable the conductive land and the terminal pattern to pass safely. The cable structure is moved in the axial direction, to contain the cable structure in the elongated tube and to position the cable connector outside the second longitudinal end.

Furthermore, there is a step of, after containment in the elongated tube, tearing off the advancing tip from the circuit board along a tear line.

Consequently, important elements of a circuit board can be safely moved for penetration in an elongated tube of the endoscope apparatus in an assembling operation, because the advancing end can operate for directing the entirety of the cable connector in a proper orientation without unwanted shifts.

BRIEF DESCRIPTION OF THE DRAWINGS

The above objects and advantages of the present invention will become more apparent from the following detailed description when read in connection with the accompanying drawings, in which:

FIG. 7 is a perspective view illustrating one preferred cable connector with which a socket connector is couplable in a transverse direction of the circuit board;

FIG. 8 is a perspective view illustrating another preferred cable connector in which an advancing tip is tearable away;

DETAILED DESCRIPTION OF THE PREFERRED EMBODIMENT(S) OF THE PRESENT INVENTION

Figure 1:
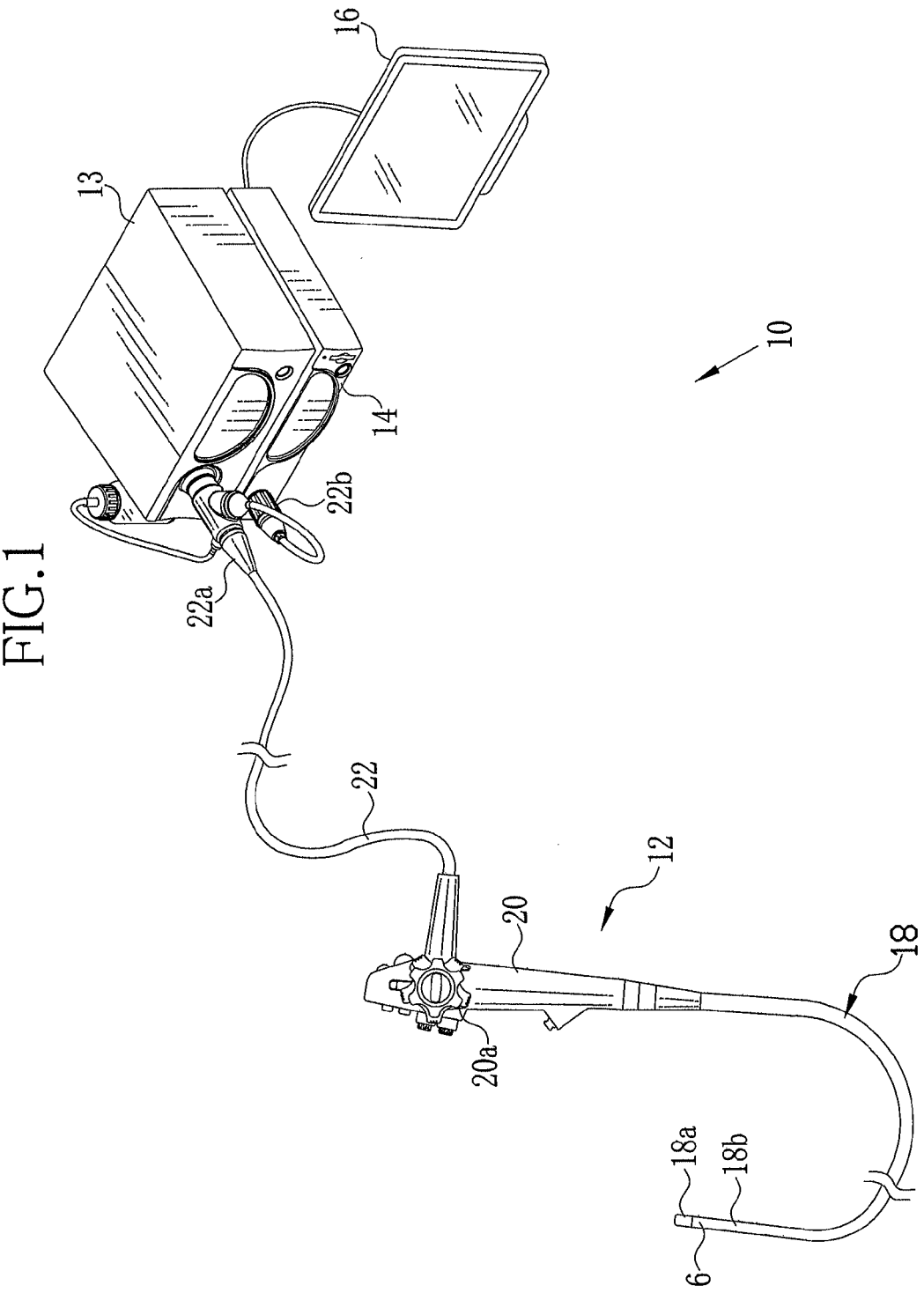
FIG. 1 is a perspective view illustrating an endoscope system.

In FIG. 1, an endoscope system 10 includes an electronic endoscope apparatus 12, alight source apparatus 13, a processing apparatus 14 and a monitor display panel 16. The endoscope apparatus 12 includes an elongated tube 18 and a handle device 20. The elongated tube 18 is entered in a body cavity of a patient, for example, gastrointestinal tract. The handle device 20 is disposed at a proximal end of the elongated tube 18. A universal cord 22 extends from the handle device 20 for connection to the light source apparatus 13 and the processing apparatus 14.

A light source is incorporated in the light source apparatus 13. The elongated tube 18 has a tip device 18a (end shell). Light from the light source is guided by a light guide device extending through the universal cord 22, the handle device 20 and the elongated tube 18 toward the tip device 18a. Lighting windows are formed in the tip device 18a, and emit the light in a distal direction.

Figure 2:
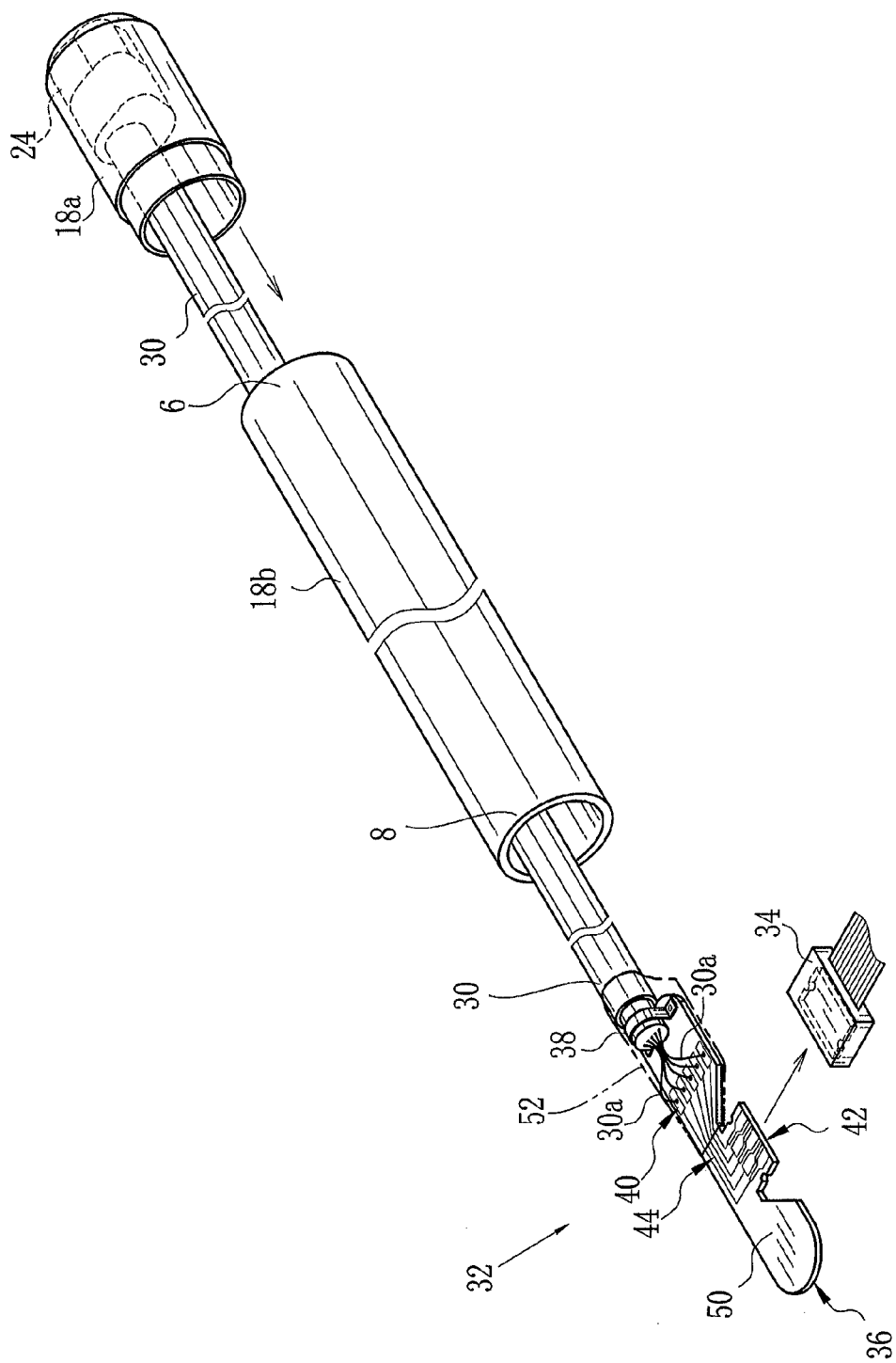
FIG. 2 is a perspective view illustrating a cable structure, an elongated tube and a socket connector in the course of penetration.

In FIG. 2, an imaging window is disposed in the tip device 18a. A camera module 24 as circuit device or electrical device is incorporated in the tip device 18a and behind the imaging window, and is an imaging unit having components of a lens system, an image sensor and the like.

In FIG. 1, rotatable steering wheels 20a are disposed on the handle device 20 for bending the elongated tube 18 up and down and to the right and left. When the steering wheels 20a are rotated, a direction of the tip device 18a for imaging with the camera module 24 is adjusted.

A cable structure 30 or line device of FIG. 2 extends from the camera module 24. The cable structure 30 penetrates through the elongated tube 18, the handle device 20 and the universal cord 22. There are connection plugs 22a and 22b at the front end of the universal cord 22. A universal cable portion of the cable structure 30 extends toward the inside of the connection plugs 22a and 22b. A socket connector 34 or mating connector is disposed in the connection plug 22b. The cable structure 30 is connected to the socket connector 34 by use of a cable connector 32 or board connector to be described later.

As the universal cord 22 is connected to the processing apparatus 14, the camera module 24 is on-line with the processing apparatus 14 through the cable structure 30. The cable structure 30 is used for the processing apparatus 14 to supply power and transmit and receive signals, so that the processing apparatus 14 controls and drives the camera module 24 for imaging. When an image is obtained, the display panel 16 is driven by the processing apparatus 14 to display the image.

In FIG. 2, a flexible tube device 18b or tubular housing is attached to a proximal end of the tip device 18a. The flexible tube device 18b receives penetration of the cable structure 30. Originally, the flexible tube device 18b is prepared separately from the tip device 18a. After the cable structure 30 is penetrated into the flexible tube device 18b, the tip device 18a is attached to the flexible tube device 18b.

The cable connector 32 is disposed at a distal end of the cable structure 30. The cable structure 30 is penetrated through a first longitudinal end 6 of the flexible tube device 18b by advancing the cable connector 32. The cable connector 32 passes through a second longitudinal end 8 of the elongated tube 18, the handle device 20 and the universal cord 22 and reaches the connection plug 22b of the universal cord 22. The cable connector 32 is mechanically coupled with (plugged in) the socket connector 34 disposed in the connection plug 22b.

The universal cord 22 includes a cover tube (not shown) through which the universal cable portion and the light guide device extend.

Figure 3:
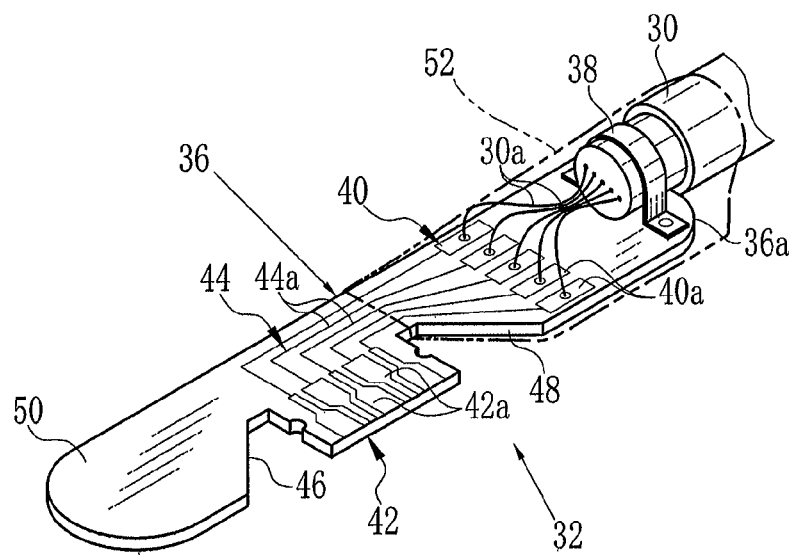
FIG. 3 is a perspective view illustrating a cable connector.

In FIG. 3, the cable connector 32 includes a circuit board 36 (substrate board) and a retainer 38 for retaining the cable structure 30 on the circuit board 36. The circuit board 36 is formed from rigid material. The circuit board 36 is a long plate extending in the axial direction, and has a smaller width than an inner diameter of the flexible tube device 18b for easy passage through the flexible tube device 18b.

A front end of the cable structure 30 is attached to a rear end of the circuit board 36. The retainer 38 squeezes the cable structure 30 with an upper surface of the circuit board 36 for firm attachment. Plural signal lines 30a constitute the cable structure 30.

Various circuit elements are mounted on the upper surface of the circuit board 36, including a land pattern 40, a terminal pattern 42 (signal connection interface), and a wiring pattern 44. The land pattern 40 includes several conductive lands 40a, and is disposed at a rear end of the circuit board 36. The signal lines 30a are electrically coupled to the conductive lands 40a by soldering or the like. The terminal pattern 42 includes plural terminals 42a arranged along a longer side line of the circuit board 36. The wiring pattern 44 includes plural wiring lines 44a printed on the circuit board 36. The terminals 42a are electrically coupled to the conductive lands 40a by the wiring lines 44a.

A protection packaging 52 or cover is disposed around the land pattern 40 and the signal lines 30a for covering. An example of the protection packaging 52 is a heat contraction tube. A size of the protection packaging 52 is large enough to cover the signal lines 30a and the land pattern 40. However, the protection packaging 52 may have a large size for covering the terminal pattern 42 additionally. After entry of the cable connector 32 through the flexible tube device 18b, a portion of the protection packaging 52 covering the terminal pattern 42 is torn away to peel the terminal pattern 42. The protection packaging 52 is illustrated in FIGS. 2 and 3 but not in the remaining drawings for simplicity.

To couple the cable connector 32 with the socket connector 34, the circuit board 36 is moved in a direction for advancing the terminal pattern 42 into the socket connector 34. Terminals (not shown) in the socket connector 34 come in contact with the terminals 42a to couple the cable connector 32 with the socket connector 34 for electrical conduction.

A pair of cutouts 46 and 48 are formed in the circuit board 36 and disposed on its longer side line. The cutouts 46 and 48 are arranged in the longitudinal direction of the circuit board 36, and operate for preventing interference of walls of the socket connector 34 in the course of coupling the cable connector 32 with the socket connector 34.

The cutout 46 has a tapered shape with a surface inclined in a direction to increase its depth toward the center of the circuit board 36 in its transverse direction. The cutout 48 has a tapered shape with a surface inclined in a direction to increase its depth symmetrically with the cutout 46. Thus, the cutouts 46 and 48 guide the socket connector 34 toward a position of a predetermined depth of the circuit board 36 in the course of coupling the cable connector 32 with the socket connector 34 by plug-in.

In the circuit board 36, an advancing tip 50 or tab for guide and protection is disposed on a front side from the terminal pattern 42. The advancing tip 50 is defined by extending the circuit board 36 in the forward direction on the side of the conductive lands 40a. The advancing tip 50 prevents the conductive lands 40a of the circuit board 36 from being damaged or scratched in the course of passage through the flexible tube device 18b. The advancing tip 50 with a curved edge has a shape with a decreasing width in the forward direction for reducing resistance of the flexible tube device 18b for entry. Also, flexibility of the advancing tip 50 is high because of its decreasing width.

The form of the advancing tip 50 with the circuit board 36 is effective in preventing occurrence of damages and scratches on the land pattern 40, the terminal pattern 42, the wiring pattern 44 and the signal lines 30a in the course of passage from the first longitudinal end 6 to the second longitudinal end 8 through the flexible tube device 18b. Should the advancing tip 50 be broken, the remaining elements of the circuit board 36 can be protected from breakage by the presence of the advancing tip 50. Also, the advancing tip 50 enables the circuit board 36 to pass smoothly through the flexible tube device 18b owing to its decreasing width.

The cutouts 46 and 48 in the circuit board 36 are effective in structurally reducing a width of the cable connector 32 in comparison with a cable connector in which a terminal group protrudes laterally from its longer side line. An area of the terminal pattern 42 can be defined within a profile line of the circuit board 36.

A tapered guide surface 36a is formed at a rear end of the cable connector 32, curved arcuately, and utilized for guiding in the course of disassembling the cable connector 32. The cable connector 32 can be pulled and disassembled safely by use of the guide surface 36a for the purpose of maintenance, because the guide surface 36a prevents the cable connector 32 from interference with the inner surface of the flexible tube device 18b.

The present invention is not limited to the above embodiment. For example, the conductive lands 40a are disposed at the rear end of the circuit board. The terminal pattern is disposed on a front side from the conductive lands 40a. However, the terminal pattern may be disposed at the rear end of the circuit board. The conductive lands 40a may be disposed on a front side from the terminal pattern.

Figure 4:
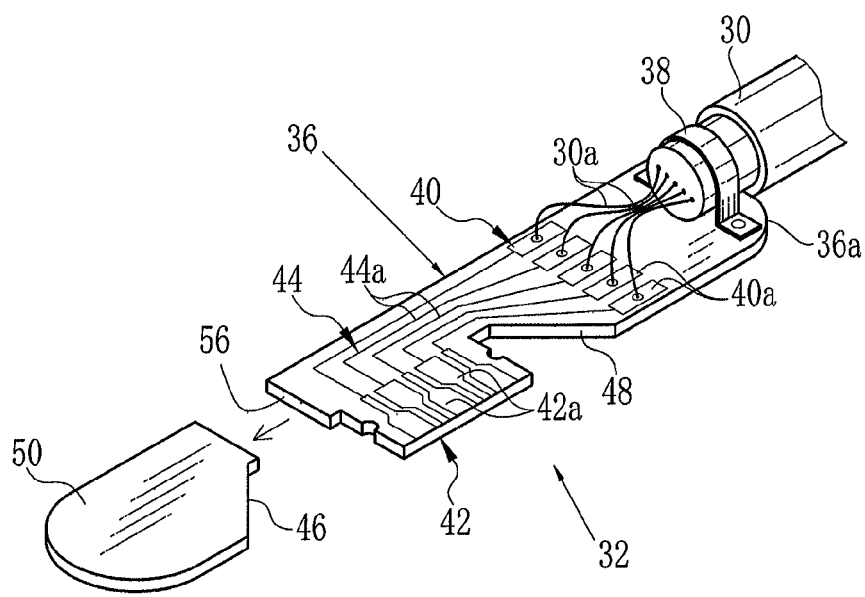
FIG. 4 is a perspective view illustrating another preferred cable connector in which an advancing tip is tearable away.

In FIG. 4, another preferred embodiment of the circuit board 36 has the advancing tip 50 as a tear tab of a tearable form along a tear line 56. After the circuit board 36 is penetrated through the flexible tube device 18b, the advancing tip 50 is torn off from the circuit board 36, which is then coupled with the socket connector 34. Elements similar to those of the above embodiment are designated with identical reference numerals.

As the circuit board 36 is coupled with the socket connector 34 after tearing off the advancing tip 50, no inner space is required for disposing the advancing tip 50 around the socket connector 34. A construction relevant to the socket connector 34 can have a reduced size. Also, the portion for tearing the advancing tip 50 is weaker than its remaining portions because of the cutout 46. It is possible to tear off the advancing tip 50 easily, and prevent improper breakage of the remaining portions of the circuit board 36.

Figure 5:
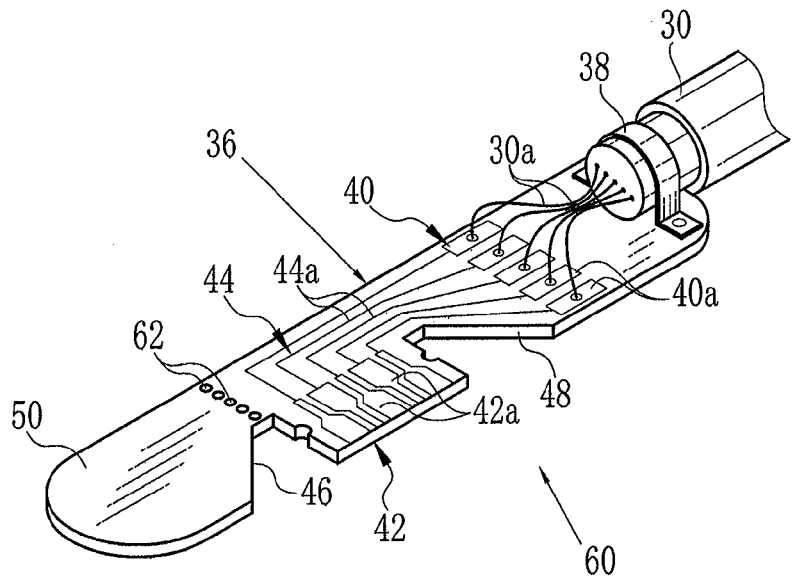
FIG. 5 is a perspective view illustrating one preferred cable connector in which a cutout and perforations are formed along a tear line.
Figure 6:
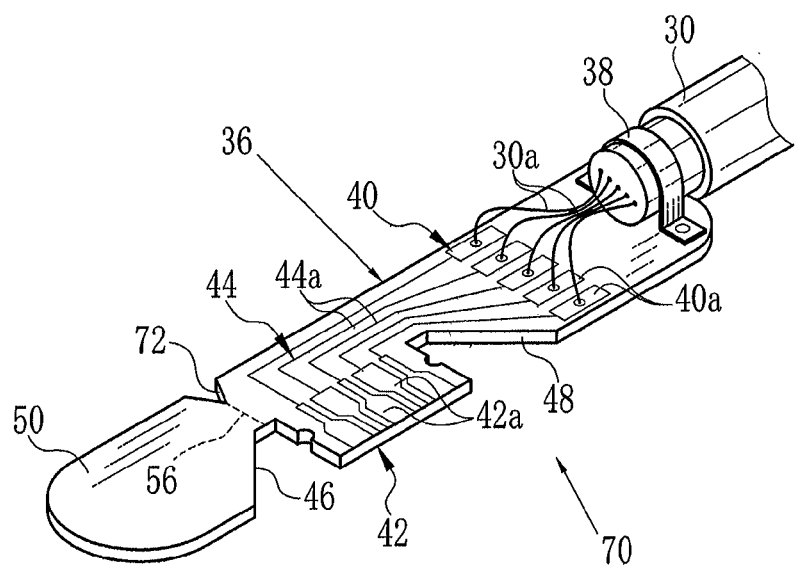
FIG. 6 is a perspective view illustrating still another preferred cable connector in which an advancing tip has a cutout and a notch.

Mechanical strength of a portion of the tear line can be lowered structurally to facilitate tear-off. In FIG. 5, one preferred cable connector 60 or board connector includes perforations 62 or openings, which are arranged along a tear line for smaller strength. In FIG. 6, still another preferred cable connector 70 includes a notch 72 at an end of a tear line. Various forms for small strength of a tear line can be used, including a groove, recess and the like.

In FIG. 7, one preferred cable connector 80 is illustrated, and does not have a cutout. A circuit board 82 (substrate board) of the cable connector 80 includes a terminal pattern 86 (signal connection interface), where terminals 84 are arranged in the transverse direction of the circuit board 82. In combination with the cable connector 80, a socket connector 88 is a type in a fork shape with upper and lower ridges for capturing the circuit board 82. Note that it is possible for a cable connector to have the terminals arranged in the longitudinal direction of the circuit board and not to have a cutout.

Figure 9:
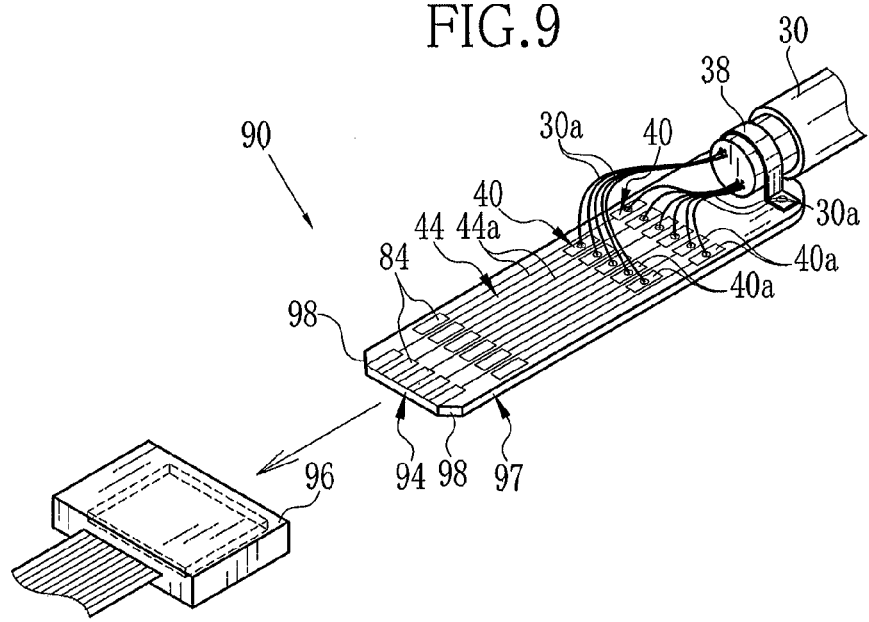
FIG. 9 is a perspective view illustrating the cable connector of FIG. 8 in a state after tear-off.

In FIGS. 8 and 9, another preferred cable connector 90 includes an advancing tip 92 or tear tab for protection, which is used for changeover between an entry condition and a couplable condition where the cable connector 90 is couplable with a socket connector 96. A circuit board 94 is moved forwards for coupling of the cable connector 90. If the advancing tip 92 remains as illustrated in FIG. 8, a terminal pattern 97 cannot enter the socket connector 96 and is prevented from electrical connection with the socket connector 96 by blocking of the advancing tip 92. Two notches 98 along a tear line are formed in the circuit board 94. When the circuit board 94 is torn along the tear line at the notches 98, the advancing tip 92 is torn off to allow coupling of the circuit board 94. The terminal pattern 97 enters the socket connector 96 to couple the circuit board 94 with the socket connector 96 connectively.

Figure 10:
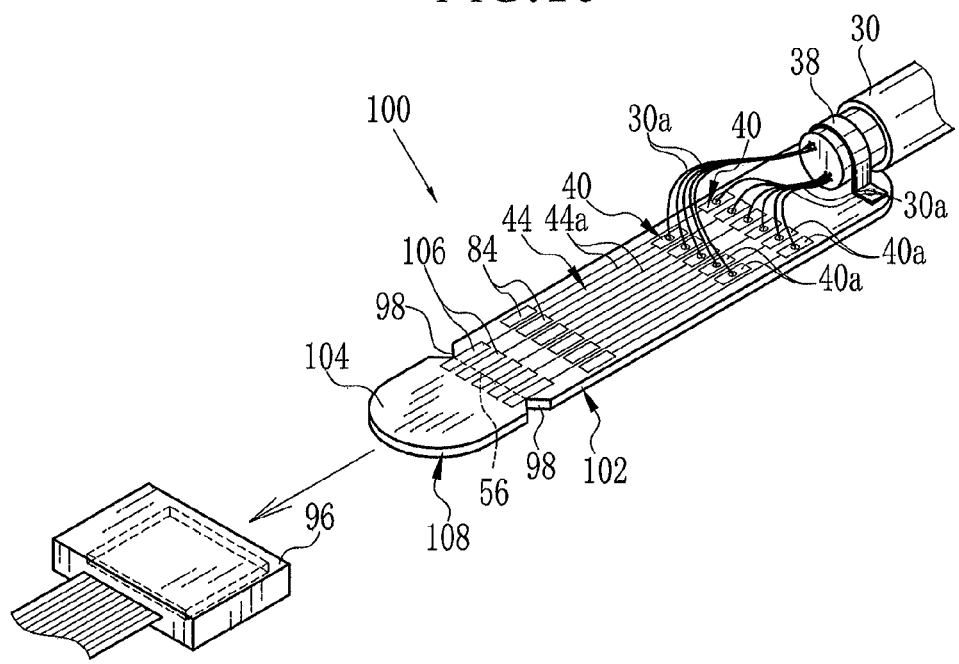
FIG. 10 is a perspective view illustrating one preferred cable connector in which notches for a tear line are disposed beside a terminal pattern.

In FIG. 10, one preferred cable connector 100 includes terminals 106 which are originally arranged along the tear line 56 defined between the notches 98. A circuit board 108 has a terminal pattern 102 and an advancing tip 104, which is torn off along the tear line 56. Should an edge formed by tearing the circuit board 108 be changed finely, the terminals 106 become positioned at the front end of the circuit board 108 after the tear-off. It is possible to prevent failure in the electrical connection due to mispositioning the terminals at the front end of the circuit board.

Figure 11:
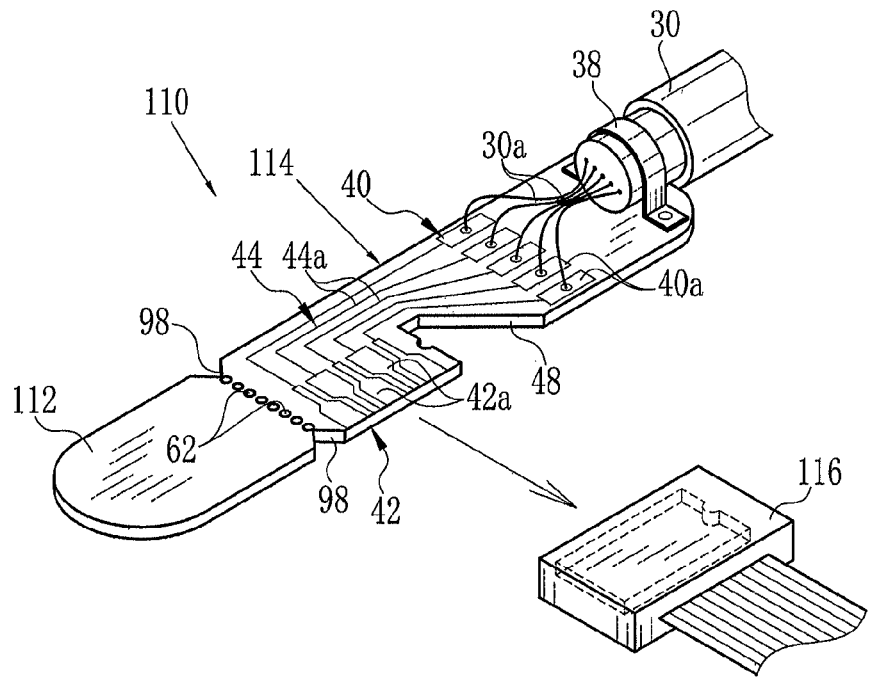
FIG. 11 is a perspective view illustrating still another preferred cable connector in which perforations are formed along a tear line.

In FIG. 11, still another preferred cable connector 110 is shaped to move a circuit board 114 in the transverse direction for coupling with a socket connector 116. An advancing tip 112 of the circuit board 114 operates in the same manner as that of FIGS. 8-10. The notches 98 are disposed along a tear line defined between the advancing tip 112 and the terminal pattern 42.

Figure 12:
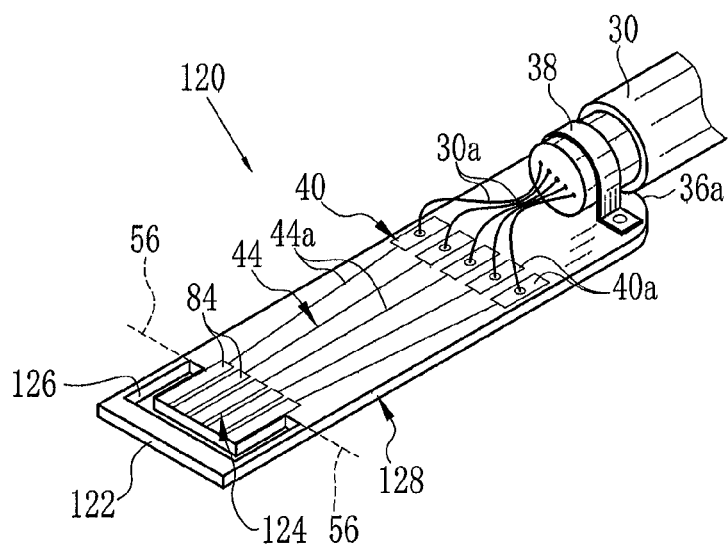
FIG. 12 is a perspective view illustrating one preferred cable connector having an opening in a channel shape.

In FIG. 12, one preferred cable connector 120 includes an opening 126 in a channel shape. A circuit board 128 includes a terminal pattern 124 (signal connection interface), and an advancing tip 122 or front portion. The opening 126 is disposed on a line between the terminal pattern 124 and the advancing tip 122. The advancing tip 122 is also formed to extend in a channel shape. In the circuit board 128 of the cable connector 120, the advancing tip 122 can be easily torn off. No uneven surface will be created on front and lateral edges of the terminal pattern 124 upon tearing off the advancing tip 122. Suitability for coupling of the cable connector 120 with a socket connector can be maintained without drop. Also, the advancing tip 122 is ready to deform owing to the opening 126 in the cable connector 120. The advancing tip 122 has higher flexibility than remaining portions of the circuit board 128. Therefore, damages to the terminal pattern 124 and main portions of the circuit board 128 can be prevented reliably according to their higher resistance to shock.

Note that an opening for imparting flexibility is not limited to the opening 126 in the cable connector, but can be modified for the purpose. Also, various examples of methods for determining high flexibility of the advancing tip can be utilized, including forming of an opening as described above, forming a tip end with a decreasing width, using a material for the advancing tip different from a material for the terminal pattern, and using a highly flexible material for the circuit board in combination of a reinforcing plate attached to the circuit board for high strength.

Figure 13:
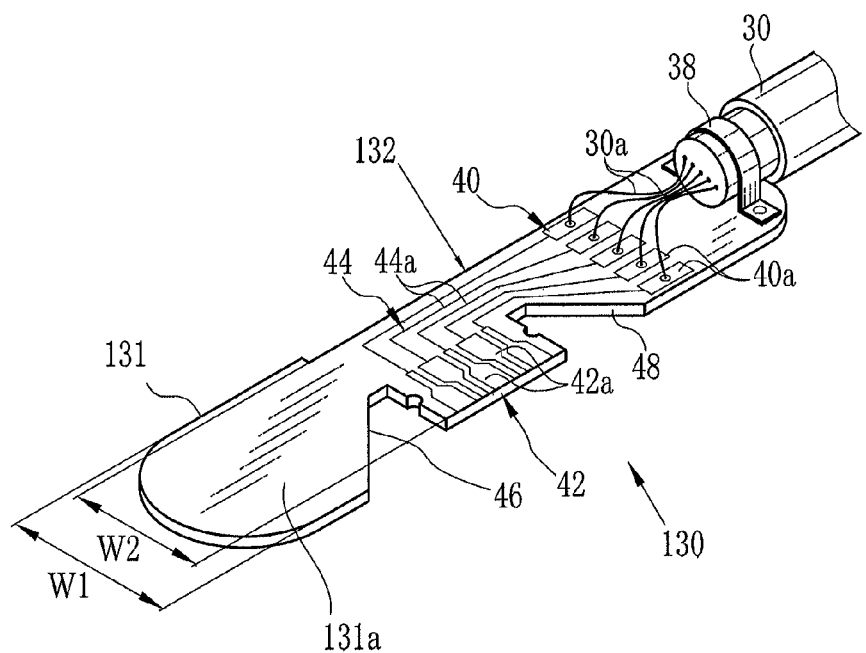
FIG. 13 is a perspective view illustrating another preferred cable connector in which an advancing tip has a widest section with a maximum width.
Figure 14:
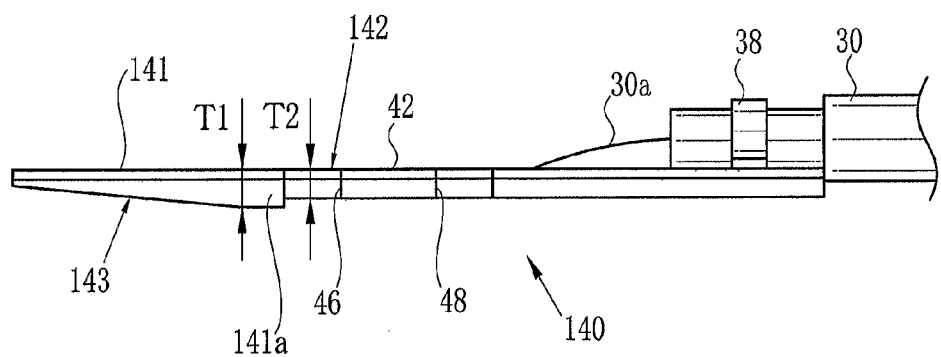
FIG. 14 is a side elevation illustrating one preferred cable connector in which an advancing tip has a thickest section with a maximum thickness.

In FIG. 13, another preferred cable connector 130 or board connector includes an advancing tip 131 or tab for protection with a greater width W1 than a width W2 of a circuit board 132. A widest section 131a of the cable connector 130 is disposed in the advancing tip 131. In FIG. 14, one preferred cable connector 140 includes an advancing tip 141 with a greater thickness T1 than a thickness T2 of a circuit board 142 (substrate board). A thickest section 141a of the cable connector 140 is disposed in the advancing tip 141. For this shape, an additional plate 143 for adjusting the thickness is attached to the circuit board 142. Also, the circuit board 142 can be formed originally with a gradually increasing thickness. The widest section 131a of the advancing tip 131 and the thickest section 141a of the advancing tip 141 are effective in reliably advancing in the penetration.

Figure 15:
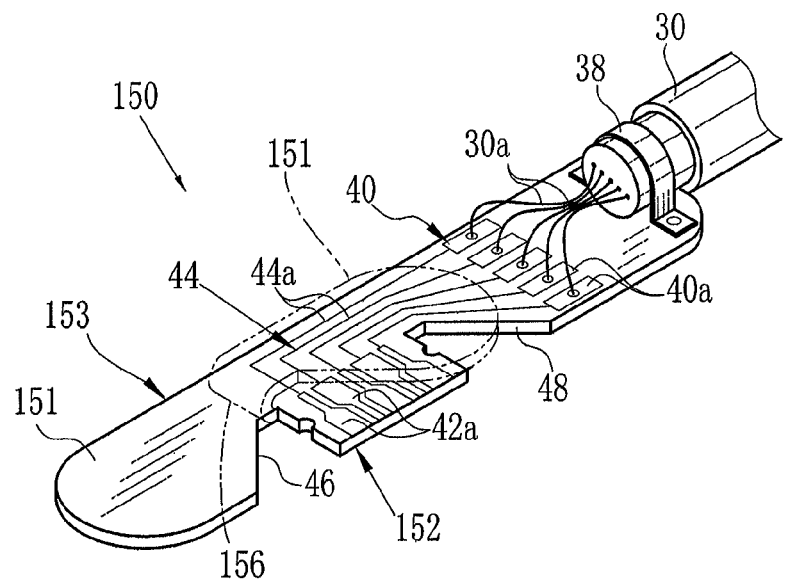
FIG. 15 is a perspective view illustrating still another preferred cable connector in which an advancing tip is bendable back.

In FIG. 15, still another preferred cable connector 150 has a bendable advancing tip 151. The cable connector 150 has a circuit board 153, and a terminal pattern 152 (signal connection interface). A bend line 156 is predetermined between the terminal pattern 152 and the advancing tip 151, which is bent back to cover and protect the terminal pattern 152. To this end, an example of the circuit board 153 is a flexible wiring board with such a thickness that the circuit board 153 will not deform even in entry of the cable connector 150 through the flexible tube device 18b. Also, the circuit board 153 may be a rigid circuit board without flexibility, and may have the bend line 156 formed in the rigid circuit board with a groove or the like for allowing bend of the rigid circuit board. The advancing tip 151 is bent back to overlap on the circuit board 153, so that a space for containing the advancing tip 151 can be set small. For the maintenance, the cable connector 150 is pulled and disassembled from the flexible tube device 18b of FIG. 2. Then the cable connector 150 is reentered in the flexible tube device 18b for reassembling. The advancing tip 151 can be extended readily in a straight form, and therefore is effective in facilitating the reentry of the cable structure 30. A size of the advancing tip 151 is predetermined suitably in compliance with a size of relevant portions to be protected. Furthermore, it is possible for the advancing tip 151 to cover the wiring pattern 44, the land pattern 40, the signal lines 30a and the like in addition to the terminal pattern 152.

Note that the cutout 46 in the cable connector 150 can be in a shape different from the tapered shape, for example, slit shape or the like to facilitate the bendback with smaller strength. Also, the cutout 46 may be omitted.

Also, it is possible initially to bend back the bendable tab 151 (tip) before entry of the bendable tab 151 in the flexible tube device 18b so as to protect the terminal pattern 152 in the course of the initial penetration. The advancing tip is constituted by the portion of the bend line 156.

Figure 16:
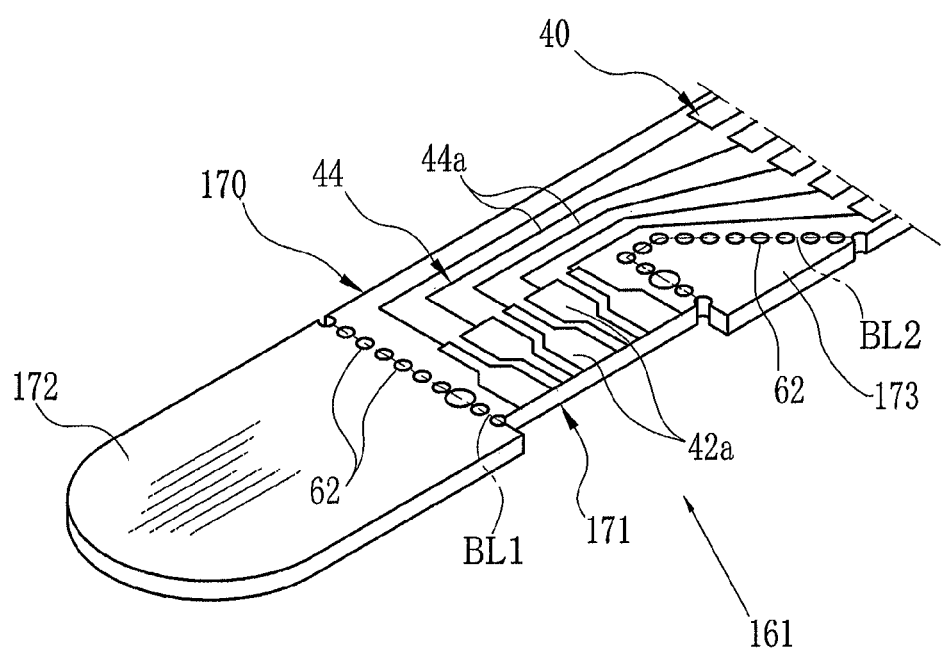
FIG. 16 is a perspective view illustrating one preferred cable connector in which a tearable unused region is formed in a circuit board.

In FIGS. 16-19, other preferred cable connectors 161, 162, 163 and 164 are illustrated, in which each terminal pattern is disposed internally. In FIG. 16, a terminal pattern 171 (signal connection interface) has an edge disposed to retreat from a longer side line of a circuit board 170. Tear lines BL1 and BL2 are formed beside the terminal pattern 171. The perforations 62 are arranged on the tear lines BL1 and BL2. An advancing tip 172 or tab is tearable from the circuit board 170 along the tear line BL1. Also, a tearable unused region 173 is torn off from the circuit board 170 along the tear line BL2, to form a cutout for coupling with the socket connector 34 of FIG. 2.

Figure 17:
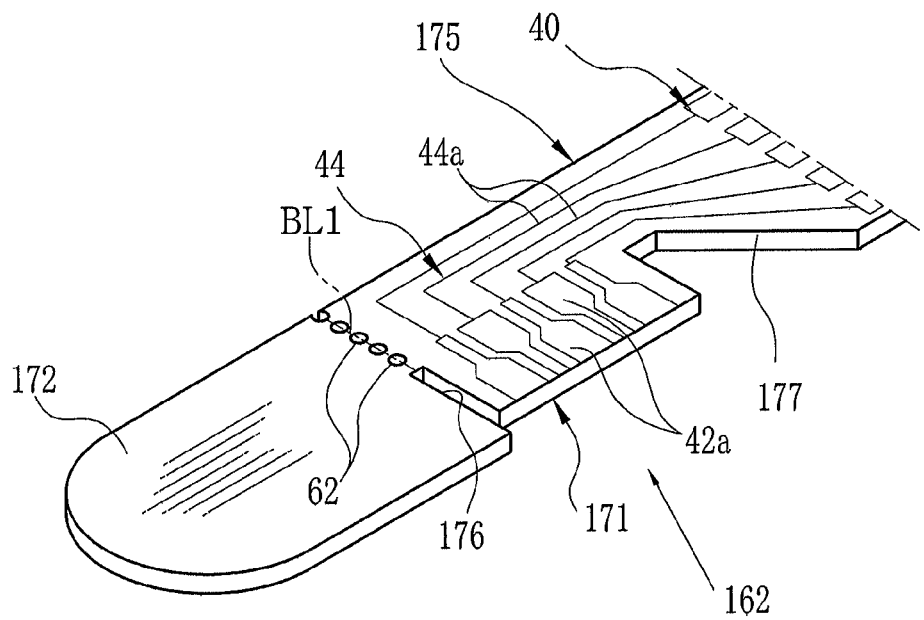
FIG. 17 is a perspective view illustrating still another preferred cable connector in which a linear slit is formed together with perforations.
Figure 18:
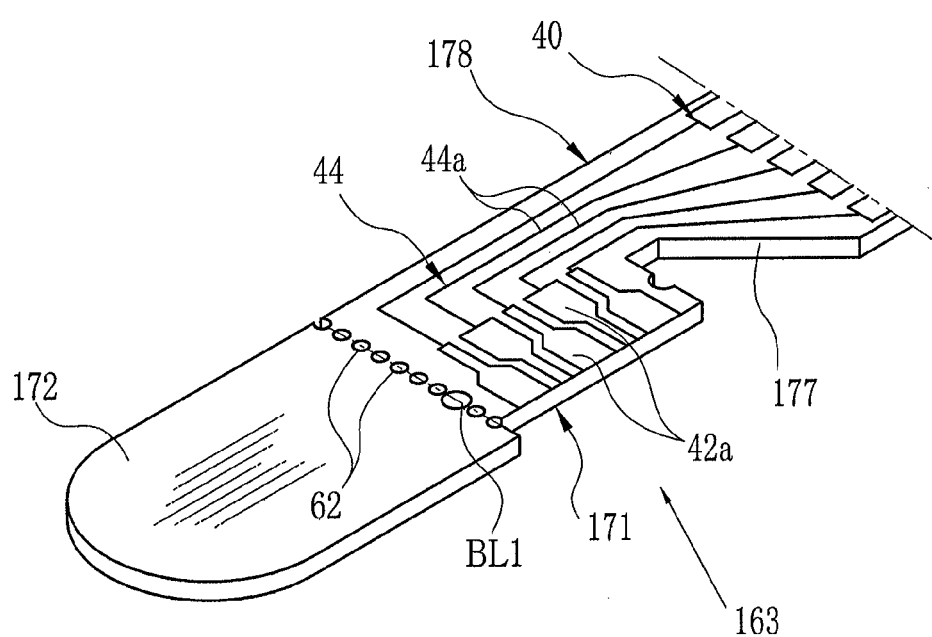
FIG. 18 is a perspective view illustrating one preferred cable connector in which the perforations of a single series are formed.

In FIG. 17, the cable connector 162 includes a circuit board 175, a linear slit 176 (cutout) and a cutout 177. The linear slit 176 is formed on an extension of the tear line BL1. The cutout 177 is formed originally in the manner after tear-off on the tear line BL2 of FIG. 16. In the cable connector 163 of FIG. 18, the cable connector 162 is repeated but with a difference in that the linear slit 176 is not formed. A circuit board 178 includes the cutout 177 on the rear side. The perforations 62 are arranged on the tear line BL1 fully in the transverse direction.

Note that the linear slit 176 may have a very fine width smaller than depicted in FIG. 17. A notch can be formed instead of the linear slit 176.

Figure 19:
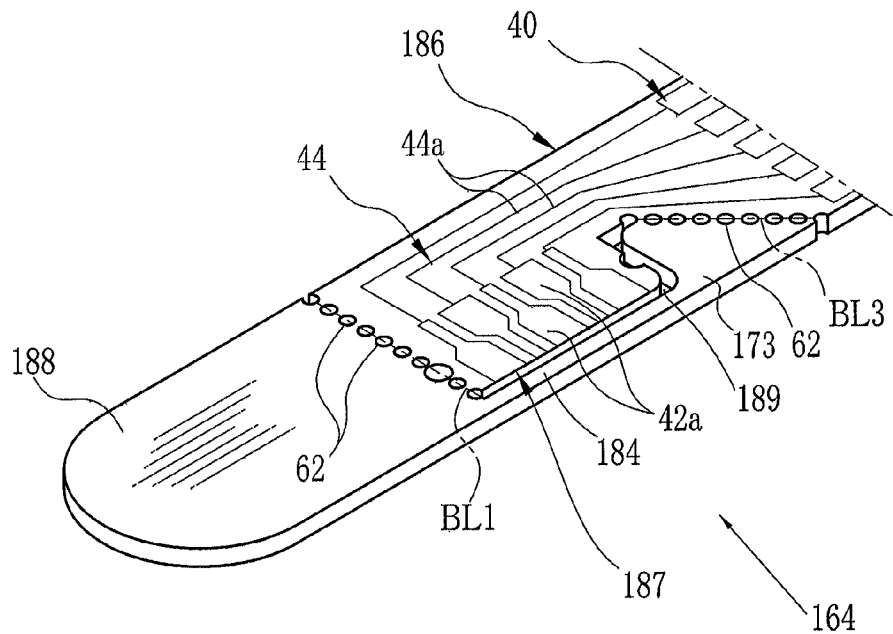
FIG. 19 is a perspective view illustrating another preferred cable connector in which an extension from an advancing tip is disposed beside a terminal pattern.

In FIG. 19, the cable connector 164 has an advancing tip 188 with a spacer region 184 extending toward the rear side. The cable connector 164 has a circuit board 186, a terminal pattern 187 (signal connection interface), and a separation opening 189 (slit) in an L shape. The spacer region 184 projecting from the advancing tip 188 is disposed beside the terminal pattern 187 in the transverse direction. The separation opening 189 is previously formed between the terminal pattern 187 and the spacer region 184. After the cable connector 164 is penetrated through the flexible tube device 18b in FIG. 2, the advancing tip 188 is torn off from the circuit board 186 along tear lines BL1 and BL3, so that the terminal pattern 187 can be coupled to the socket connector 34 connectively. The presence of the advancing tip 188 on the periphery of the terminal pattern 187 can prevent the terminal pattern 187 from interference with an inner surface of the flexible tube device 18b and prevent deformation or damages of the terminal pattern 187.

In the embodiment, the advancing tip 188 is torn off together with the spacer region 184 and the unused region 173. However, an additional tear line may be formed in the transverse direction so that the spacer region 184, the unused region 173 and the advancing tip 188 can be separated from the circuit board 186 discretely from one another.

Figure 20:
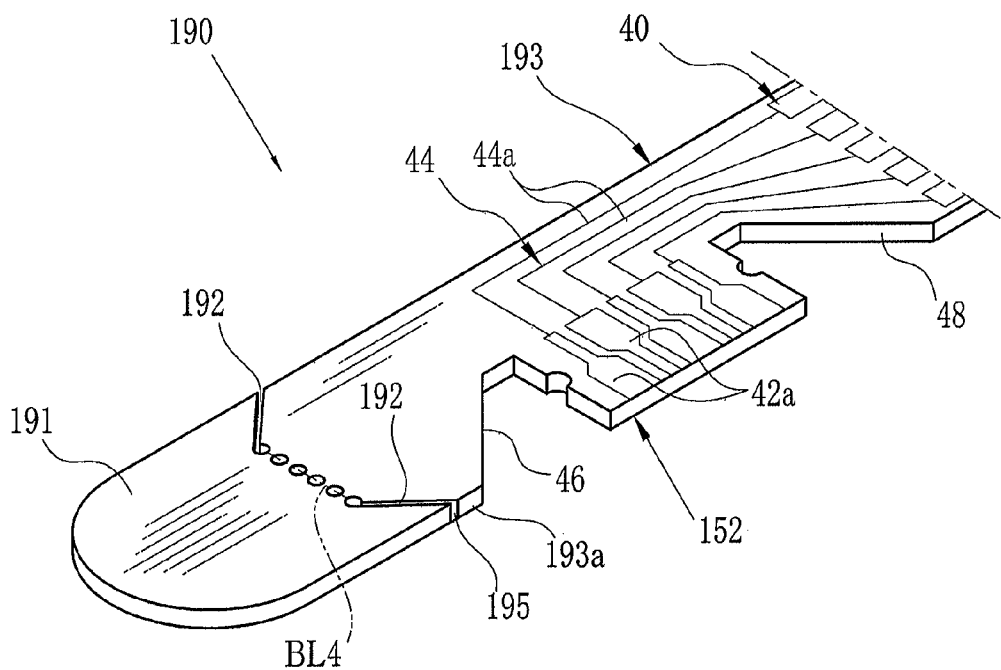
FIG. 20 is a perspective view illustrating one preferred cable connector in which linear slits are formed in an advancing tip.

In FIG. 20, another preferred cable connector 190 includes a circuit board 193, an advancing tip 191 and linear slits 192 (cutouts). The advancing tip 191 is tearable from the circuit board 193 along the tear line BL4 with the linear slits 192. If the tip end of the circuit board 193 is deformed with projections inside the flexible tube device 18b or bent sharply, the advancing tip 191 is torn off along the tear line BL4. The circuit board 193 has a longer side line 193a, on which the linear slits 192 are inclined. When the advancing tip 191 is torn off from the circuit board 193 along the tear line BL4, a residual region with a tapered guide surface 195 is created with an inclination, and operates for guiding in the reentry in the flexible tube device 18b. Thus, the cable connector 190 can be returned into the flexible tube device 18b easily after the maintenance. Note that the recesses 192 may be formed in a curved shape instead of the linear shape.

In the embodiment of FIG. 20, the side edge of the terminal pattern is positioned to retreat from the longer side line 193a of the circuit board 193. However, the side edge of the terminal pattern extending in the axial direction can be collinear with the longer side line 193a of the circuit board 193.

Also, additional perforations may be arranged in place of the linear slits 192. The perforations 62 on the tear line BL4 and the additional perforations can be arranged in such a U shape that a residual region after the tear-off can have a width decreasing in the axial direction.

Figure 21:
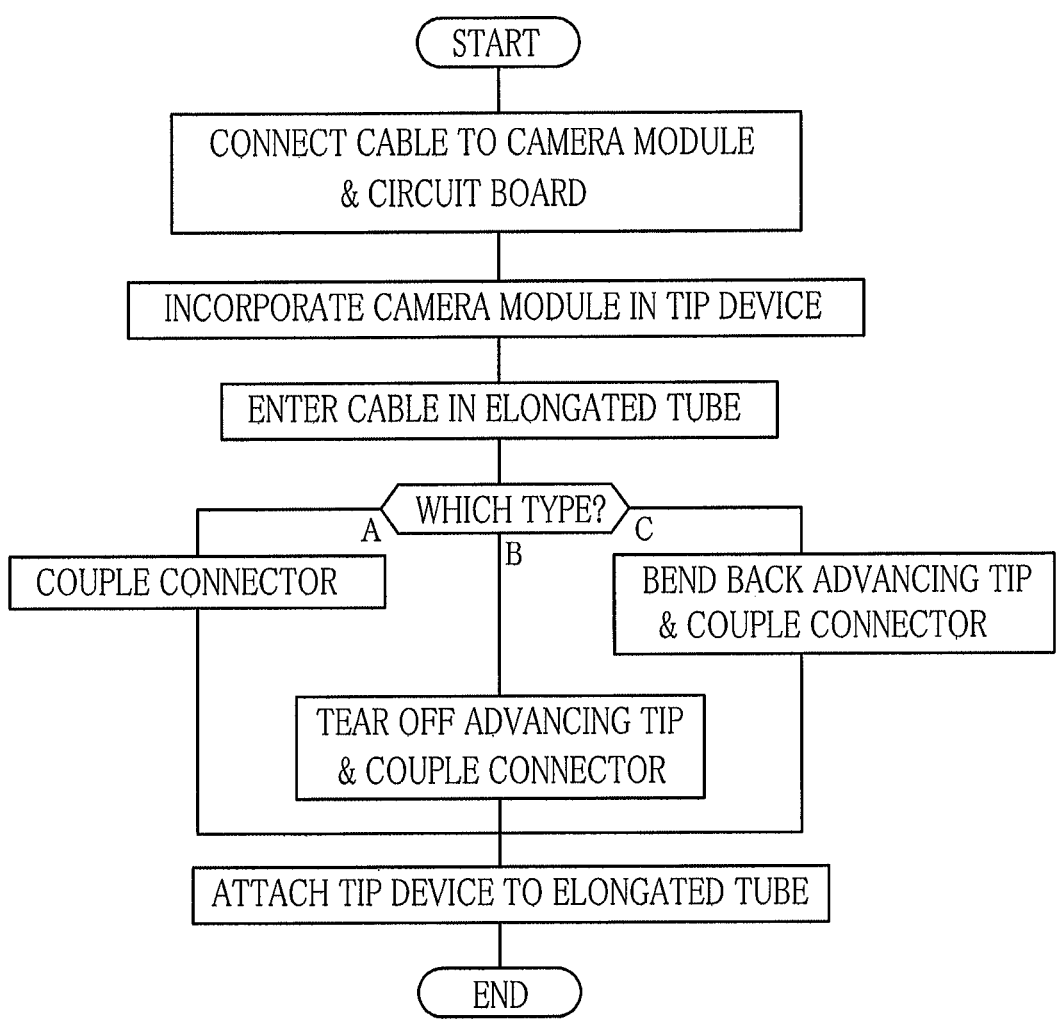
FIG. 21 is a flow chart illustrating a method of producing the endoscope apparatus.

In FIG. 21, production of the endoscope apparatus with the cable connector of the invention is illustrated. At first, first end portions of the signal lines 30a in the cable structure are coupled to a circuit board in the camera module by soldering. Then second end portions (front) of the signal lines 30a of the cable structure 30 are electrically coupled to the conductive lands 40a of the cable connector 32 as illustrated in FIG. 3. Also, the cable structure 30 is fixed on the circuit board 36 by the retainer 38.

The camera module 24 becomes incorporated in the tip device 18a. See FIG. 2. Then the cable connector 32 is advanced and entered in the flexible tube device 18b. A pull wire (not shown) is used and has been penetrated in the flexible tube device 18b. A first end of the pull wire is firmly fastened to a portion between the advancing tip 50 and the terminal pattern 42, and connected to the cable connector 32. A second end of the pull wire is pulled manually to penetrate the cable connector 32 through the flexible tube device 18b.

After penetration of the cable structure 30 through the flexible tube device 18b, the socket connector 34 is coupled with the terminal pattern 42 connectively in manners different between types A, B and C of the cable connector. In Type A, the advancing tip 50 remains without separation. In the cable connector 32 of FIG. 2, the socket connector 34 is combined with the terminal pattern 42. Then the flexible tube device 18b is connected to the tip device 18a.

Type B is the examples of FIGS. 4-6, 9-14 and 16-20. The advancing tip 50, 92, 104, 112, 122, 131, 141, 172, 188 or 191 is torn off from the cable connector 32, 60, 70, 90, 100, 110, 120, 130, 140, 161-164 or 190. After the tear-off, the socket connector 34 is coupled with the terminal pattern 42.

An example of type C is the cable connector 150 in FIG. 15. The advancing tip 151 is bent back to cover main portions of the circuit board 153. Then the terminal pattern 152 of the cable connector 150 is coupled with the socket connector. It is also possible to bend back the advancing tip 151 after coupling of the terminal pattern 152 with the socket connector.

Note that the position of the coupling between the cable connector and the socket connector (mating connector) is changeable with high degree of freedom. It is possible in the invention to couple the cable connector with a socket connector inside the handle device or the processing apparatus. Also, a circuit board (substrate board) in the cable connector is not limited to the plate shape, but can be in a cylindrical or prismatic shape or the like.

Figure 22:
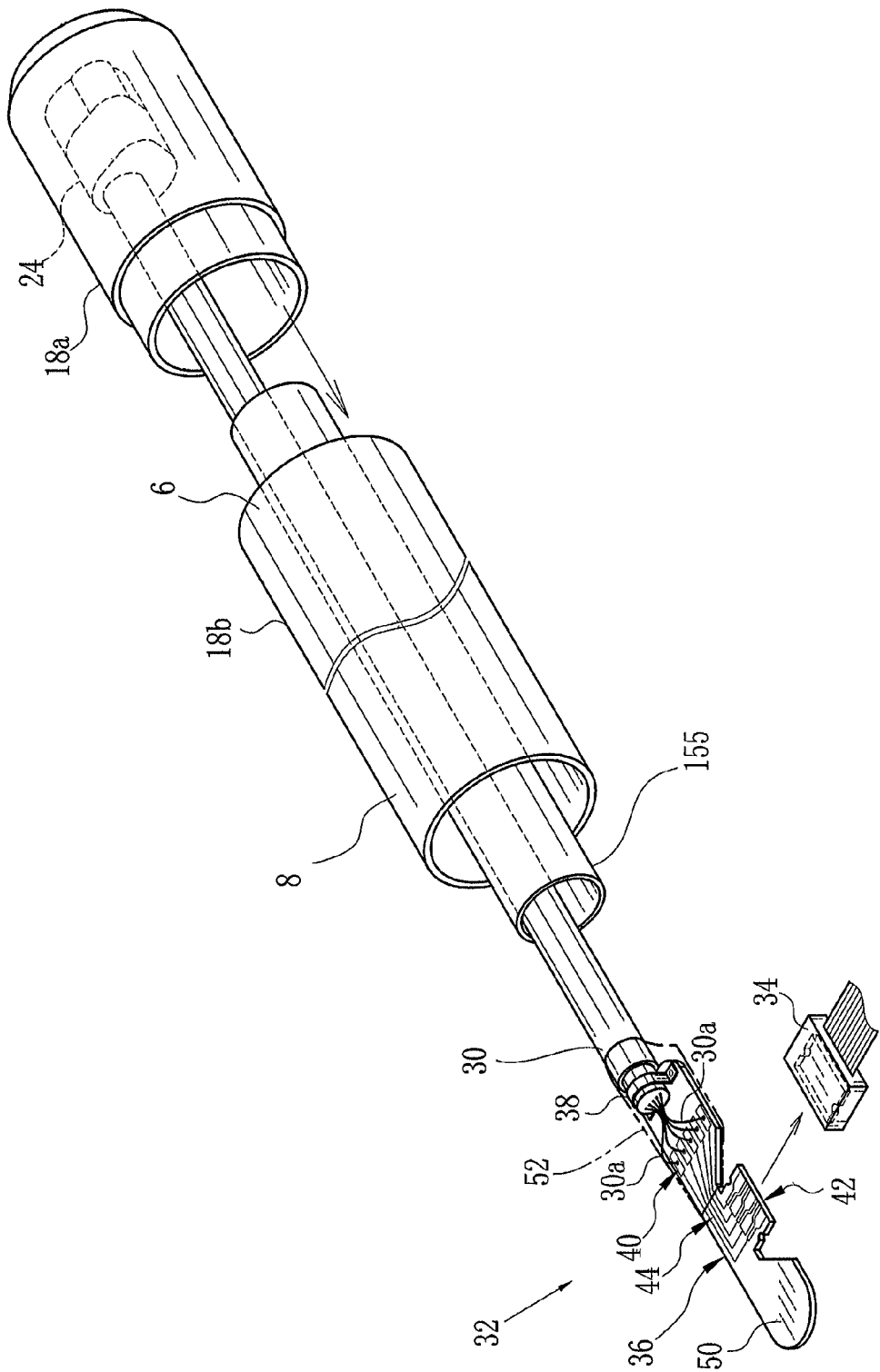
FIG. 22 is a perspective view illustrating the cable structure, the elongated tube and the socket connector in combination with a protection tube.

Although the cable connector 32 and the cable structure 30 are directly penetrated through the elongated tube 18 in the above embodiments, the cable connector 32 and the cable structure 30 can be passed through a protection tube 155 of FIG. 22, working channel or the like provided in the elongated tube 18. For this structure, the cable connector 32 and the cable structure 30 can be entered directly in the protection tube 155, working channel or the like without a guide mechanism, because the resiliency of the cable structure 30 can be utilized.

In the above embodiments, the camera module 24 is incorporated in the tip device 18a. However, the camera module 24 may be incorporated in a portion of the elongated tube 18 on a proximal side from the tip device 18a. For this structure, an imaging window, a lens, a light guide device and the like are incorporated in the tip device 18a for receiving object light.

In the above embodiments, the endoscope apparatus includes the camera module for imaging optically. However, a tube apparatus of the invention may be an ultrasonic endoscope having an ultrasonic transducer, catheter, probe or the like. An endoscope apparatus of the invention may be for industrial use without medical use. Also, a cable connector may be used for a device of various types other than an endoscope apparatus, and can be used with a cable passed through a tube of a small diameter.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A cable connector for an endoscope apparatus including an elongated tube disposed to extend in an axial direction, a circuit device incorporated in said elongated tube, and a cable structure, including plural signal lines, having first and second ends, said first end being connected to said circuit device, wherein said cable connector is connected with said second end, and coupleable with a socket connector connectively, said cable connector comprising:

a circuit board having a predetermined width in a manner passable through said elongated tube in said axial direction;

a conductive land formed on said circuit board, and coupled to said second end;

a terminal pattern, formed on said circuit board, for connective coupling by reception in said socket connector;

an advancing tip, formed on a front side of said circuit board in said axial direction, for initially advancing upon entry of said circuit board in said elongated tube, to enable said conductive land and said terminal pattern to pass safely, wherein said advancing tip includes a widest section, formed on a front side of said circuit board in said axial direction, and having a maximum width, and said advancing tip further includes a tapered section, formed on a front side of said widest section, and having a decreasing width.

2. The cable connector as defined in claim 1, wherein flexibility of said advancing tip is higher than flexibility of a portion of said circuit board on a rear side from said advancing tip.

3. The cable connector as defined in claim 1, wherein said circuit device is an imaging unit for generating an image signal according to object light from a body cavity.

4. The cable connector as defined in claim 1, wherein said advancing tip has a width decreasing in said axial direction.

5. The cable connector as defined in claim 1, wherein said conductive land is disposed at a rear end of said circuit board in said axial direction.

6. The cable connector as defined in claim 1, further comprising a bend line formed in said circuit board on a rear side from said advancing tip, wherein said advancing tip is overlapped on at least said terminal pattern by bending said circuit board along said bend line.

7. The cable connector as defined in claim 1, wherein said terminal pattern includes plural terminals arranged on a longer side line of said circuit board extending in said axial direction.

8. The cable connector as defined in claim 1, wherein said terminal pattern includes plural terminals arranged in a transverse direction of said circuit board.

9. The cable connector as defined in claim 1, wherein said endoscope includes a handle device, mounted on a proximal end of said elongated tube, for partially containing said cable structure;
said cable structure includes a universal cable portion, disposed to extend further from said handle device in said axial direction, and having said second end.

10. A cable connector for an endoscope apparatus including an elongated tube disposed to extend in an axial direction, a circuit device incorporated in said elongated tube, and a cable structure, including plural signal lines, having first and second ends, said first end being connected to said circuit device, wherein said cable connector is connected with said second end, and coupleable with a socket connector connectively, said cable connector comprising:
a circuit board having a predetermined width in a manner passable through said elongated tube in said axial direction;
a conductive land formed on said circuit board, and coupled to said second end;
a terminal pattern, formed on said circuit board, for connective coupling by reception in said socket connector;
an advancing tip, formed on a front side of said circuit board in said axial direction, for initially advancing upon entry of said circuit board in said elongated tube, to enable said conductive land and said terminal pattern to pass safely, wherein said advancing tip includes a thickest section, formed on a front side of said circuit board in said axial direction, and having a maximum thickness.

11. A cable connector for an endoscope apparatus including an elongated tube disposed to extend in an axial direction, a circuit device incorporated in said elongated tube, and a cable structure, including plural signal lines, having first and second ends, said first end being connected to said circuit device, wherein said cable connector is connected with said second end, and coupleable with a socket connector connectively, said cable connector comprising:
a circuit board having a predetermined width in a manner passable through said elongated tube in said axial direction;
a conductive land formed on said circuit board, and coupled to said second end;
a terminal pattern, formed on said circuit board, for connective coupling by reception in said socket connector;
an advancing tip, formed on a front side of said circuit board in said axial direction, for initially advancing upon entry of said circuit board in said elongated tube, to enable said conductive land and said terminal pattern to pass safely, wherein the cable connector further comprises a tear line, disposed in said circuit board on a rear side from said advancing tip, and adapted for tearing off said advancing tip after containment in said elongated tube.

12. The cable connector as defined in claim 11, wherein a portion of said tear line has a lower strength than a remaining portion of said circuit board.

13. The cable connector as defined in claim 11, further comprising first and second notches, formed in respectively first and second longer side lines of said circuit board extending in said axial direction, and disposed at respectively ends of said tear line.

14. A cable connector for an endoscope apparatus including an elongated tube disposed to extend in an axial direction, a circuit device incorporated in said elongated tube, and a cable structure, including plural signal lines, having first and second ends, said first end being connected to said circuit device, wherein said cable connector is connected with said second end, and coupleable with a socket connector connectively, said cable connector comprising:
a circuit board having a predetermined width in a manner passable through said elongated tube in said axial direction;
a conductive land formed on said circuit board, and coupled to said second end;
a terminal pattern, formed on said circuit board, for connective coupling by reception in said socket connector;
an advancing tip, formed on a front side of said circuit board in said axial direction, for initially advancing upon entry of said circuit board in said elongated tube, to enable said conductive land and said terminal pattern to pass safely, wherein the cable connector further comprises a pair of cutouts, formed in a longer side line of said circuit board extending in said axial direction, so positioned that said terminal pattern is disposed therebetween, for preventing interference with a wall of said socket connector in coupling of said terminal pattern with said socket connector.

15. A cable connector for an endoscope apparatus including an elongated tube disposed to extend in an axial direction, a circuit device incorporated in said elongated tube, and a cable structure, including plural signal lines, having first and second ends, said first end being connected to said circuit device, wherein said cable connector is connected with said second end, and coupleable with a socket connector connectively, said cable connector comprising:
a circuit board having a predetermined width in a manner passable through said elongated tube in said axial direction;
a conductive land formed on said circuit board, and coupled to said second end;
a terminal pattern, formed on said circuit board, for connective coupling by reception in said socket connector;

an advancing tip, formed on a front side of said circuit board in said axial direction, for initially advancing upon entry of said circuit board in said elongated tube, to enable said conductive land and said terminal pattern to pass safely, wherein the cable connector further comprises, a first cutout, disposed in said circuit board on a rear side from said advancing tip, and formed in a first longer side line of said circuit board extending in said axial direction;

a tear line, disposed to extend from said first cutout in a transverse direction of said circuit board, and adapted for tearing off said advancing tip after containment in said elongated tube;

a second cutout, disposed in said circuit board on a rear side from said terminal pattern, formed in said first longer said line, for preventing interference with a wall of said socket connector in coupling of said terminal pattern with said socket connector.

16. A cable connector for an endoscope apparatus including an elongated tube disposed to extend in an axial direction, a circuit device incorporated in said elongated tube, and a cable structure, including plural signal lines, having first and second ends, said first end being connected to said circuit device, wherein said cable connector is connected with said second end, and coupleable with a socket connector connectively, said cable connector comprising:

a circuit board having a predetermined width in a manner passable through said elongated tube in said axial direction;

a conductive land formed on said circuit board, and coupled to said second end;

a terminal pattern, formed on said circuit board, for connective coupling by reception in said socket connector;

an advancing tip, formed on a front side of said circuit board in said axial direction, for initially advancing upon entry of said circuit board in said elongated tube, to enable said conductive land and said terminal pattern to pass safely, wherein the cable connector further comprises an opening formed in said circuit board between said advancing tip and said terminal pattern;

said opening including:
a first open area disposed to extend in a transverse direction of said circuit board;
second and third open areas, disposed to extend from respectively first and second ends of said first open area toward a rear side, and so positioned that said terminal pattern is disposed therebetween.

17. A producing method of producing an endoscope apparatus including an elongated tube disposed to extend in an axial direction, and having a first longitudinal end on a distal side and a second longitudinal end on a proximal side, a circuit device incorporated in said elongated tube, a cable structure, including plural signal lines, having first and second ends, said first end being connected to said circuit device, and a cable connector, connected with said second end, and coupleable with a socket connector electrically, said producing method comprising steps of:

connecting said first end with said circuit device;
connecting said second end with said cable connector;
advancing said cable connector into said first longitudinal end, wherein said cable connector includes a circuit board having a predetermined width in a manner passable through said elongated tube in said axial direction, a conductive land formed on said circuit board, and coupled to said second end, a terminal pattern, formed on said circuit board, for connective coupling by reception in said socket connector, and an advancing tip, formed on a front side of said circuit board in said axial direction, for initially advancing upon entry of said circuit board in said elongated tube, to enable said conductive land and said terminal pattern to pass safely;

moving said cable structure in said axial direction, to contain said cable structure in said elongated tube and to position said cable connector outside said second longitudinal end, further comprising a step of, after containment in said elongated tube, tearing off said advancing tip from said circuit board along a tear line.

* * * * *